United States Patent
DiGregorio et al.

(10) Patent No.: US 8,313,455 B2
(45) Date of Patent: Nov. 20, 2012

(54) SYRINGES WITH A REDUCED SUSCEPTIBILITY TO FREEZE-THAW VOID FORMATION AND METHODS OF MANUFACTURING SUCH SYRINGES

(75) Inventors: Henry DiGregorio, Westerly, RI (US); David Foote, San Jose, CA (US); James Getty, Vacaville, CA (US)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 13/482,286

(22) Filed: May 29, 2012

(65) Prior Publication Data

US 2012/0234720 A1 Sep. 20, 2012

Related U.S. Application Data

(62) Division of application No. 12/251,642, filed on Oct. 15, 2008, now Pat. No. 8,231,568.

(60) Provisional application No. 60/980,196, filed on Oct. 16, 2007.

(51) Int. Cl.
*A61M 37/00* (2006.01)
*B01J 19/08* (2006.01)

(52) U.S. Cl. .......... 604/90; 427/578; 427/534; 428/35.7

(58) Field of Classification Search .................... 604/90; 427/578, 534; 428/35.7
See application file for complete search history.

(56) References Cited

U.S. PATENT DOCUMENTS

| | | | |
|---|---|---|---|
| 2,591,046 A * | 4/1952 | Brown | 604/90 |
| 4,846,796 A | 7/1989 | Carrell et al. | |
| 4,979,656 A | 12/1990 | Looker | |
| 5,016,784 A | 5/1991 | Batson | |
| 5,242,405 A | 9/1993 | Howe | |
| 5,326,603 A | 7/1994 | Van Dyke et al. | |
| 5,686,238 A | 11/1997 | Martinson et al. | |
| 5,743,401 A | 4/1998 | Takahashi | |
| 5,765,722 A | 6/1998 | Beebe et al. | |
| 5,779,668 A | 7/1998 | Grabenkort | |
| 5,783,867 A | 7/1998 | Belke et al. | |
| 5,788,670 A * | 8/1998 | Reinhard et al. | 604/89 |
| 5,827,456 A | 10/1998 | Bergner et al. | |
| 5,971,953 A * | 10/1999 | Bachynsky | 604/90 |
| 6,386,396 B1 | 5/2002 | Strecker | |
| 6,558,764 B2 | 5/2003 | Blom et al. | |
| 6,573,122 B2 | 6/2003 | Standing | |
| 6,616,019 B2 | 9/2003 | D'Alessio et al. | |
| 6,685,063 B2 | 2/2004 | Brugner | |
| 6,691,895 B2 | 2/2004 | Strecker | |
| 6,881,462 B2 | 4/2005 | Mullins et al. | |
| 2004/0108334 A1 | 6/2004 | Strecker | |
| 2005/0221035 A1 | 10/2005 | Wyatt | |
| 2005/0236063 A1 | 10/2005 | DiGregorio et al. | |

FOREIGN PATENT DOCUMENTS

| | | |
|---|---|---|
| DE | 3113491 A1 | 1/1983 |
| DE | 3624638 A1 | 2/1988 |
| DE | 19513240 C1 | 6/1996 |
| DE | 20101440 U1 | 7/2001 |
| EP | 0196288 A2 | 10/1986 |
| FR | 2686864 A1 | 8/1993 |
| GB | 2305160 A | 4/1997 |
| JP | 8057051 A | 3/1996 |
| WO | 03101862 A1 | 12/2003 |
| WO | 2005108242 A1 | 11/2005 |

OTHER PUBLICATIONS

Office Action in related U.S. Appl. No. 10/829,126 dated Jul. 13, 2007; 9 pages; USPTO.
Office Action in related U.S. Appl. No. 10/829,126 dated Apr. 8, 2008; 10 pages; USPTO.
Office Action in related U.S. Appl. No. 10/829,126 dated Jul. 22, 2008; 4 pages; USPTO.
European Patent Office, International Search Report & Written Opinion issued in corresponding PCT Application serial No. PCT/US2005/013058 dated Sep. 13, 2005, 10 pages.
European Patent Office, International Preliminary Report on Patentability issued in corresponding PCT Application serial No. PCT/US2005/013058 dated Jul. 21, 2006, 5 pages.
European Patent Office, International Search Report issued in corresponding European Application serial No. 05006798 dated May 29, 2008, 3 pages.
Emerson & Cuming, a National Starch & Chemical Company, "Technical Tip Handling Frozen Adhesives", 2000 (4 pages).
EFD, a Nordson Company, "Engineered Fluid Dispensing the Optimum™ Cartridge System", product brochure, 2007 (8 pages).
EFD, a Nordson Company, "Engineered Fluid Dispensing Optimum (TM)", product brochure, 2007 (8 pages).
EFD, a Nordson Company, "Precision Dispense Tips", technical brochure, 2005 (2 pages).
EFD, a Nordson Company, "Ultra 2400 Series Dispensing Workstation", product brochure, 2006, 4 pages.
USPTO, Notice of Allowance issued in related U.S. Appl. No. 12/251,642 dated May 24, 2012.
USPTO, Office Action issued in related U.S. Appl. No. 12/251,642 dated Dec. 23, 2011.

* cited by examiner

*Primary Examiner* — Robert D. Harlan
(74) *Attorney, Agent, or Firm* — Wood, Herron & Evans, LLP

(57) ABSTRACT

Syringes for holding fluids susceptible to void formation when the syringe and fluid are frozen and thawed before use. The interior surface of the syringe barrel is modified by exposure to a plasma such that the incidence of void formation in the fluid is prevented or, at the least, significantly reduced in comparison with conventional syringes.

7 Claims, 3 Drawing Sheets

SYRINGES WITH A REDUCED SUSCEPTIBILITY TO FREEZE-THAW VOID FORMATION AND METHODS OF MANUFACTURING SUCH SYRINGES

CROSS-REFERENCE TO RELATED APPLICATIONS

This application is a divisional of application Ser. No. 12/251,642, filed Oct. 15, 2008 (pending), which claims the benefit of U.S. Provisional Application No. 60/980,196, filed Oct. 16, 2007, the disclosures of each of which is hereby incorporated by reference herein in their entirety.

BACKGROUND

This invention relates generally to syringes and, more particularly, to syringes for dispensing fluids that are frozen for storage and then thawed from the frozen state, along with the syringe, shortly before use.

Syringes containing a frozen fluid, such as premixed curable liquids, epoxies, pastes, encapsulants, underfills, dam fluids, thixotropic liquids, and adhesives, are used in semiconductor and optoelectronic packaging, as well as numerous other applications. Premixing substances like adhesives and pastes eliminates handling and weighing individual components, the mess associated with mixing, testing before and after mixing for quality assurance, and special handling problems. Syringes are also referred to by other conventional terms such as cartridge, barrel, tube, or reservoir.

The syringe is filled with fluid at room temperature and frozen at a temperature below the fluid's freezing point. The syringe and its frozen contents are shipped in a thermally insulated container from the manufacturer at a temperature of about −40° C. to about −80° C. (i.e., on dry ice). The end user stores the frozen syringe and fluid in a low-temperature freezer at a temperature below the fluid's freezing point. Low temperature storage extends the working life of the fluid, delays aging and prevents curing, which cooperate to extend or prolong the fluid shelf life. Shortly before dispensing the fluid from the syringe, the end user warms the syringe and fluid to ambient temperature, which serves to thaw the frozen fluid. After the fluid is dispensed, the syringe is discarded.

When thawed from the frozen state, conventional syringes containing such frozen fluids are susceptible to a phenomenon known as freeze-thaw voiding. Specifically, the frozen fluid and the syringe each shrink in dimensions or contract when frozen. It is believed that, because the coefficients of thermal expansion of the solid polymer material forming the syringe and the fluid differ, the degree of dimensional shrinkage differs. When warmed, the sidewall of the syringe warms at a faster rate than the frozen mass of fluid held inside the syringe, which causes the sidewall to expand before the frozen fluid. The sidewall is believed to pull away from the frozen fluid to define air-filled spaces between the frozen mass of fluid and the sidewall. As the fluid thaws and randomly re-wets regions of the syringe sidewall, the air-filled spaces are surrounded by the fluid and define air bubbles or pockets near the sidewall. The trapped air pockets, termed by some as freeze-thaw voids, adversely impact the dispensability of the fluid from the syringe. Specifically, dispensing fluid laced with air-filled voids causes dispensing inconsistencies including but not limited to tailing, dripping, dispense voids, and weight variations.

For some fluids, freeze-thaw voids are observed to form in the vast majority of fluid-filled syringes. Depending upon the fluid type, the voids may spontaneously alleviate by migrating to the vicinity of the syringe plunger and perhaps passing rearwardly between the periphery of the plunger and the bore of the barrel. For other fluid types, the voids remain stationary and, therefore, are not self-alleviating. In this circumstance, one option available to the end user is to discard the unused syringe to avoid the potential for dispensing fluid containing the voids. Another option for the end user is to cautiously dispense the fluid from the syringe without dispensing the voids. In the latter option, only a portion of the fluid is dispensed and the syringe is ultimately discarded with unused fluid remaining inside the syringe.

The industry has tried without success for years to mitigate the effect of voids that are not self-alleviated by controlled warming of the fluid and syringe. After removal from the freezer, a common approach for controlled warming is to place the frozen, filled syringes inside a thermally insulated blanket or sleeve, usually composed of a foam material. The thermally insulated sleeve slows the rate at which the frozen fluid and syringe warm toward ambient temperature. However, this conventional approach has only been moderately successful in eliminating freeze-thaw voids. Moreover, the thermally insulating sleeve needlessly consumes extra space inside the thermally insulated container used by the manufacturer to ship the syringes. If not recycled, the thermally insulating sleeve must be disposed of after use. In addition, the sleeve may not securely grip and hold the syringe, which creates the potential for the syringe to fall out of the sleeve.

In view of these and other difficulties associated with freeze-thaw voiding, it would therefore be desirable to provide a syringe for fluids that reduces or minimizes the incidence of freeze-thaw voiding.

SUMMARY

In accordance with an embodiment of the invention, a syringe is provided which is used to contain a fluid susceptible to void formation when the syringe and the fluid are frozen and thawed. The syringe comprises a tubular barrel having a cylindrical bore configured to contain the fluid. The cylindrical bore has an interior surface wetted by the fluid contained inside the cylindrical bore. The interior surface is treated with a plasma before the cylindrical bore contains the fluid. The treatment with the plasma is effective to significantly reduce or eliminate freeze-thaw void formation in the fluid when the syringe and fluid are thawed.

In specific embodiments of the invention, the plasma process may modify the surface chemistry of the interior surface, may roughen the interior surface, may remove contamination from the interior surface, or a combination of these plasma-mediated effects characteristic of surface modification. In another embodiment, the interior surface may be treated with a plasma deposition process that is effective to apply a coating. In another embodiment, the plasma deposition process forming the coating may be preceded by the plasma process that either modifies the surface chemistry of the interior surface, roughens the interior surface, removes contamination from the interior surface, or a combination of these plasma-mediated effects. The plasma-based treatments of these various different embodiments of the invention may be combined together. The surface treatment(s) may make the interior surface either more hydrophobic or more hydrophilic, in comparison with an untreated interior surface of a conventional syringe barrel. The direction of change for the wetting properties of the interior surface may be contingent on factors such as fluid type and may be tailored by selection of the control parameters for the plasma.

In another embodiment of the invention, a method is provided for manufacturing a syringe to dispense a fluid susceptible to void formation when frozen and thawed before dispensing. The method includes exposing an interior surface bounding the bore of the tubular barrel to a first plasma.

The syringes of the embodiments of the invention either eliminate or significantly reduce void formation because the plasma modification to the interior surface of the syringe barrel alters the interaction between the frozen fluid and the interior surface. As a result of the reduction or elimination of freeze-thaw voids in the thawed fluid, the yield of usable filled syringes that do not experience dispensability problems, when the temperature of the syringe and fluid is elevated to thaw the frozen fluid, is increased. By eliminating or significantly reducing void formation during thawing, the dispensability of the fluid from the syringe is improved. The syringe of the various different embodiments of the invention may be used without special handling by the end user and, after use, merely discarded. Fewer filled syringes must be discarded without dispensing the fluid or after only partially dispensing the fluid. In addition, the risk of a void degrading dispensability of the fluid is eliminated or significantly reduced. Consequently, eliminating or reducing the incidence of freeze-thaw voids in the fluid contained in the syringe minimizes fluid waste and, furthermore, minimizes dispensing errors when the dispensed fluid includes one or more entrained voids.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the embodiments of the invention.

DETAILED DESCRIPTION

Figure 1:
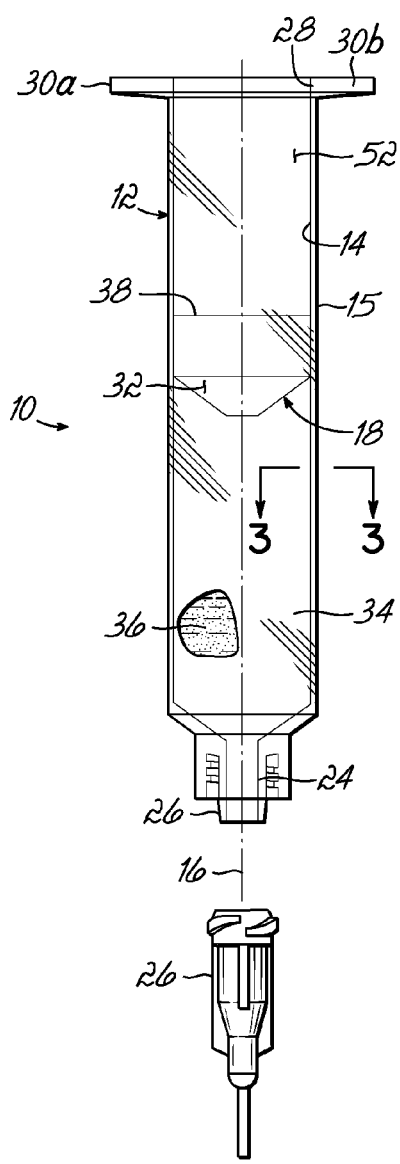
FIG. 1 is a side view of a syringe in accordance with an embodiment of the invention.
Figure 2:
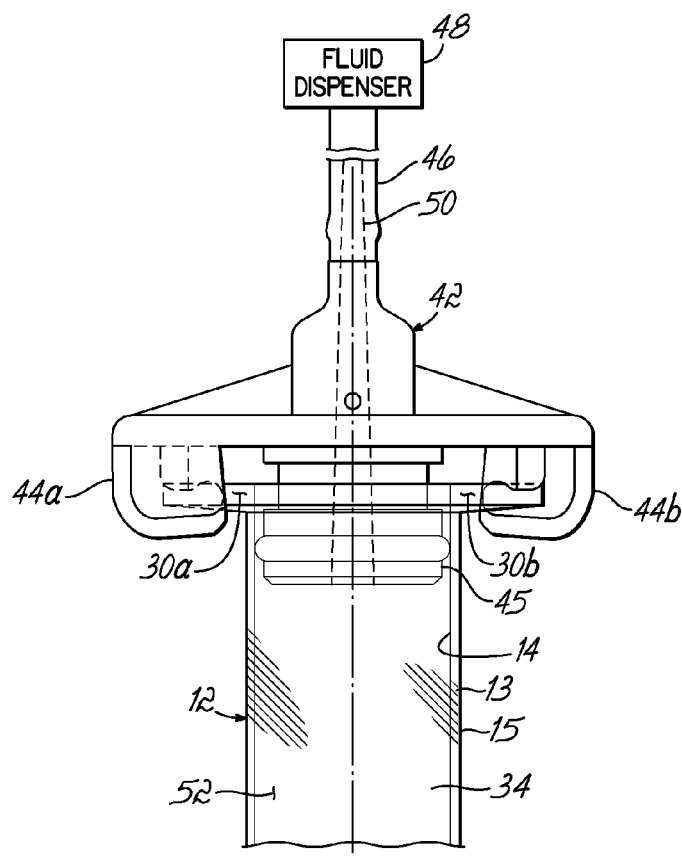
FIG. 2 is a side view of the syringe of FIG. 1 mated with an adapter effective for pneumatically coupling the syringe with a timer controller used to dispense the fluid from the syringe barrel.

With reference to FIGS. 1 and 2, a container in the representative form of a syringe 10 includes a relatively-rigid sidewall 13 defining a tubular barrel 12, a cylindrical lumen or bore 34 inside the tubular barrel 12, and a piston 18 disposed inside the cylindrical bore 34. The piston 18 or portions of the piston 18 have an interference fit with an interior surface 14 of the sidewall 13. The tubular barrel 12 is centered along a longitudinal axis 16 and the interior surface 14, which may be symmetrical about the longitudinal axis 16, represents an inner diameter of the tubular barrel 12.

The tubular barrel 12 includes a fluid outlet 24 defining a forward opening at one end of the sidewall 13 and a rearward opening 28 at an opposite end of the sidewall 13. A nozzle tip 26 is mounted to the fluid outlet 24. The hub of the nozzle tip 26 has a construction configured to provide a secure engagement with complementary structure at the fluid outlet 24 of the syringe 10. For example, the hub of the nozzle tip 26 and the fluid outlet 24 may include complementarily Luer fittings. Ears or flanges 30a,b are disposed adjacent to the rearward opening 28 of the tubular barrel 12 at a location opposite the fluid outlet 24 and project outwardly from the sidewall 13 of the tubular barrel 12.

The space or volume inside the tubular barrel 12 between a fluid-contact surface 32 of the piston 18 and the fluid outlet 24 from the tubular barrel 12 defines the reservoir inside the cylindrical bore 34. When the syringe 10 is in use, the reservoir contains an amount of a fluid 36 that is in direct contact with surface 32. The fluid 36 may be a liquid that has flow properties and that is susceptible to void formation when the syringe 10 and the fluid 36 filling the reservoir are concurrently frozen and then simultaneously thawed before use or dispensing. Included among this class of fluids 36 are pre-mixed curable liquids, epoxies, pastes, thixotropic (shear thinning) liquids, adhesives, and liquids having a viscosity ranging from 1 centipoise (cps) to 1,000,000 cps. Exemplary fluids 36 that may be stored in a frozen state in syringe 10 and that are susceptible to void formation when frozen and thawed include, but are not limited to, curable liquids, pastes and adhesives for semiconductor, microelectronics and optoelectronics packaging applications. The fluid 36 confined inside the reservoir of the cylindrical bore 34 wets the interior surface 14, as well as the fluid-contact surface 32 of the piston 18.

Although the maximum volumetric capacity of the reservoir inside the cylindrical bore 34 may vary according to a given volume specification for the syringe 10, typical volumetric capacities range from one (1) cubic centimeters (cm$^{-3}$) to seventy-five (75) cm$^{-3}$ and may specifically include volumetric capacities of 3 cm$^{-3}$, 5 cm$^{-3}$, 10 cm$^{-3}$, 30 cm$^{-3}$ and 55 cm$^{-3}$. Typical construction materials for the tubular barrel 12 and piston 18 of syringe 10 are polymers including, but not limited to, polypropylene and polyethylene, as well as blends and copolymers of these and other polymers as understood by a person having ordinary skill in the art. The tubular barrel 12 and piston 18 may be constructed from the same polymer, or from different polymers, and may be fabricated by methods, such as injection molding, understood by a person having ordinary skill in the art. The polymers constituting the tubular barrel 12 and piston 18 may include various different additives, such as light-blocking additives. For example, the tubular barrel 12 may be clear, may have a light-blocking amber configuration, or may have a light-proof black configuration. In one particular embodiment, the tubular barrel 12 is formed from a clarified polypropylene.

The non-wetted rear surface 38 of the piston 18 is accessible through the rearward opening 28 of the tubular barrel 12. The periphery of the piston 18 provides a fluid seal with the interior surface 14 so that, as the piston 18 is advanced to drive fluid 36 in the reservoir of the cylindrical bore 34 toward the fluid outlet 24, little if any fluid 36 escapes rearwardly past the piston 18 toward rearward opening 28. The piston 18 also wipes the interior surface 14 clean as the fluid 36 is dispensed. The interference fit of the piston 18 with the interior surface 14 of the tubular barrel 12 may be adjusted such that any pressure transferred from the piston 18 to the fluid 36 is quickly released when a force that is advancing piston 18 toward fluid outlet 24 is removed or discontinued.

In an alternative embodiment, the syringe 10 may have a construction modified to have the form of a cartridge. In this modified but similar construction, the flanges 30a,b are omitted from the rearward opening 28 of the tubular barrel 12. The cartridge type construction for syringe 10 may be used with additional components, such as a retainer, a retainer cap to permit coupling with the fluid dispenser 48, and an outlet cap for the fluid outlet 24.

With reference to FIGS. 1 and 2, the fluid 36 inside the reservoir of the cylindrical bore 34 is thawed and dispensed from the syringe 10 onto a product (not shown), such as a semiconductor package or an optoelectronic package. To that end, the syringe 10 is coupled by an adapter 42 with an air-powered fluid dispenser 48 typically including a microprocessor-based timer/controller. The adapter 42 has arms 44a, 44b mechanically coupled with the flanges 30a, 30b and, in addition, includes a plug 45 that is inserted into the rearward opening 28. Plug 45 has a sealed engagement with the interior surface 14.

Air pressure is supplied from the timer/controller of the fluid dispenser 48 through a passageway 50 partially in a conduit 46 and extending through the plug 45 to a headspace 52 located inside tubular barrel 12 between the adapter 42 and the piston 18. Pressurizing the headspace 52 with a sufficient air pressure overcomes the hydraulic resistance presented by the fluid 36 and the piston stiction for advancing piston 18 toward the fluid outlet 24 and thereby pressurizing the fluid 36 inside the reservoir to force amounts of the fluid 36 out of the fluid outlet 24. The air pressure supplied from the fluid dispenser 48 to the headspace 52 depends on the characteristics of the dispensed fluid 36 and may range, for example, from 0 pounds per square inch (psi) to 100 psi. Typically, the timer/controller of the fluid dispenser 48 includes a solenoid valve that is operative to control the application of air pressure to the headspace 52. The force is transferred from the piston 18 to the fluid 36 within the reservoir of the cylindrical bore 34 and amounts of the fluid 36 are expelled from the fluid outlet 24. The expelled amount of fluid 36 is based upon time control of the air pressure by the fluid dispenser 48, as well as the air pressure. Accordingly, the volume of the fluid-filled reservoir inside the cylindrical bore 34 decreases and the volume of the headspace 52 inside the tubular barrel 12 increases as fluid 36 is dispensed from the reservoir. The pressurization of the air pressure inside the headspace 52 between piston 18 and plug 45 may be optionally pulsed during the process that expels amounts of fluid 36 from fluid outlet 24.

As described hereinafter with regard to FIGS. 3 and 3A-C, the interior surface 14 of the tubular barrel 12 may be modified with a plasma treatment that changes the interaction between the frozen fluid 36 and the interior surface 14. The outcome of the plasma treatment, regardless of the particular physical manifestation caused by the plasma modification, is effective to reduce or eliminate the formation of freeze-thaw voids in the fluid 36. The outcome of the plasma treatment may depend, among other factors, on the recipe used to generate the plasma to which the interior surface 14 is exposed.

Figure 3:
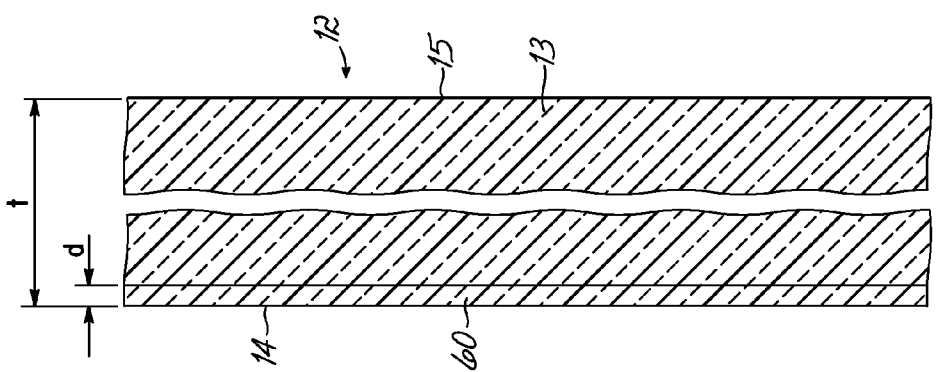
FIG. 3 is an enlarged view taken generally along line 3-3 in FIG. 1 that shows a portion of the interior surface of the syringe barrel and in which a shallow surface layer has been modified in accordance with an embodiment of the invention.

With continued reference to FIGS. 1 and 3 and in accordance with an embodiment of the invention, the interior surface 14 of the tubular barrel 12 may include a modified surface layer 60 effective to modify the interaction between interior surface 14 and the fluid 36 when interior surface 14 is wetted by the fluid 36. The modified surface layer 60, which is formed before the fluid 36 is placed in the reservoir of the cylindrical bore 34, may be effective to prevent or, at the least, significantly reduce freeze-thaw void formation in fluid 36. The modified surface layer 60 may extend from the interior surface 14 to a modified depth, d, beneath the interior surface 14, which is a minor fraction of the total thickness, t, between the interior surface 14 and an exterior surface 15 of the tubular barrel 12.

The depth, d, for the modified surface layer 60 may extend only a fraction of a monolayer into the material comprising the tubular barrel 12 or may have a greater thickness. The modification over the modified depth, d, may consist of a physical change, such as etching the interior surface 14 to generate features that change the surface morphology to introduce a surface roughness on the order of nanometers. The surface roughening is limited to a surface roughness of 10 nanometers or less. Alternatively, the modification may result in an alteration to the surface chemistry of the interior surface 14 so that the fluid 36 has a decreased hydrophobicity (i.e., an increased wettability characterized by a reduced surface tension). The exterior surface 15 may also include a modified surface layer (not shown) similar or identical to the modified surface layer 60.

In an alternative embodiment, the tubular barrel 12 may be composed of a polymer that contains an additive, or other agent or impurity, and the surface layer 60 may be depleted of the agent, relative to the bulk of the sidewall 13 of the tubular barrel 12, after the interior surface 14 is treated with the plasma.

Figure 3A:
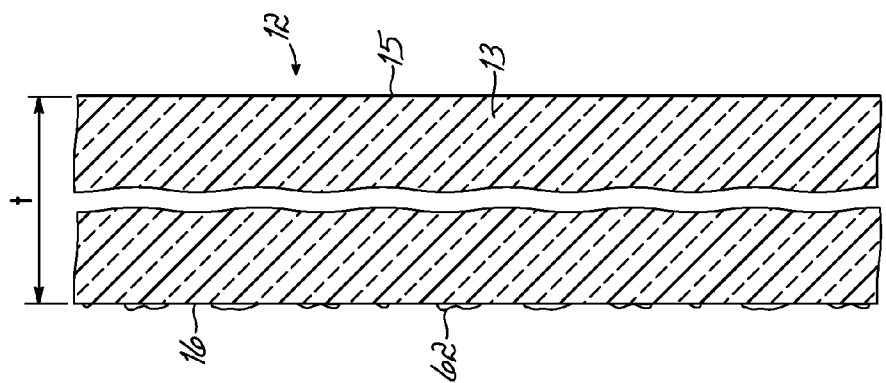
FIG. 3A is a view similar to FIG. 3 in which the interior surface of the syringe barrel is littered with contaminants.
Figure 3B:
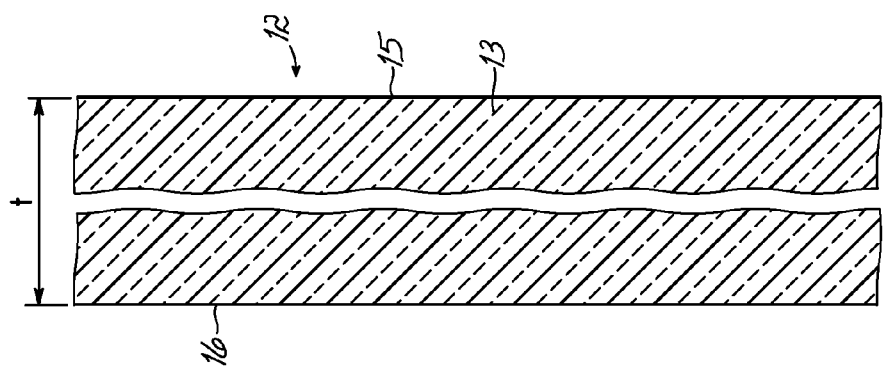
FIG. 3B is a view similar to FIG. 3A in which contaminants have been removed in accordance with an embodiment of the invention.

With reference to FIGS. 3A and 3B and in accordance with another embodiment of the invention, the interior surface 14 of the tubular barrel 12 may include contaminants 62, as shown in FIG. 3A, that originate from the fabrication process, originate from handling, or from another source. The contaminants 62 may consist of particles or other types of residue, such as a continuous or discontinuous contaminant film. The interior surface 14 may be modified, before the fluid 36 is placed in the reservoir of the cylindrical bore 34, to remove the contaminants 62, as shown in FIG. 3B. The removal of the contaminants 62 effectively modifies the interaction between interior surface 14 and the fluid 36 when interior surface 14 is wetted by the fluid 36. The removal of the contaminants 62 may be at a level effective to prevent or, at the least, significantly reduce void formation in fluid 36 when the syringe 10 and fluid 36 are frozen and thawed. The removal of the contaminants 62 may be provided either in conjunction with the modified surface layer 60 or alone. In particular, the removal of contaminants 62 may also modify the surface chemistry by changing the wetting properties of the interior surface 14. The exterior surface 15 may also have corresponding contaminants (not shown) that are removed along with contaminants 62. Alternatively, the removal of the contaminants may alter the surface chemistry of the interior surface 14 so that the interior surface 14 has a decreased hydrophobicity (i.e., an increased wettability characterized by a reduced surface tension for the fluid 36).

The contaminants 62 may be an organic substance or, alternatively, an inorganic substance such as an oxide layer or other passivation layer resulting from air exposure. The contaminants 62 may also be an additive, or other agent or impurity, contained in the polymer constituting tubular barrel 12 that blooms or otherwise migrates from the bulk of sidewall 13 to reside on the interior surface 14.

Figure 3C:
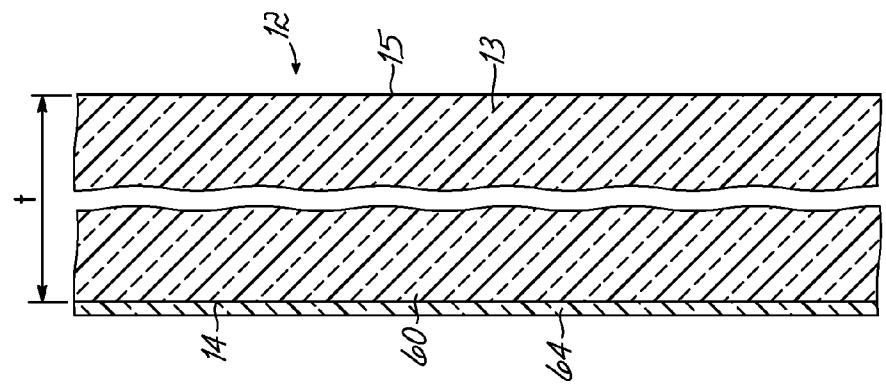
FIG. 3C is a view similar to FIG. 3 in which a coating has been applied on the interior surface of the syringe barrel in accordance with an embodiment of the invention.

With reference to FIG. 3C and in accordance with another embodiment of the invention, a coating 64 may be disposed on the interior surface 14 of the tubular barrel 12 and in direct contact with the interior surface 14 of the tubular barrel 12. The coating 64 is effective to modify the interaction between interior surface 14 and the fluid 36 when interior surface 14 is wetted by the fluid 36. The coating 64 may be applied to, or otherwise disposed on, the interior surface 14 after the contaminants 62 are removed and/or after the modified surface layer 60 is formed. The coating 64, either in combination with the modified surface layer 60, the removal of contaminants 62, both of these types of modification, or alone, may be effective to prevent or, at the least, significantly reduce freeze-thaw void formation in fluid 36 when the syringe 10 and fluid 36 are frozen and thawed. The coating 64 may be continuous, as shown in FIG. 3C, or discontinuous as, for example, islands of material at random locations and with arbitrary sizes on the interior surface 14. The coating 64 may be deposited on the interior surface 14 or, alternatively, grown so as to also incorporate material from the tubular barrel 12. The exterior surface 15 may also include a coating (not shown) similar or identical to coating 64.

In use and with reference to FIGS. 1, 2, and 3A, the reservoir of the cylindrical bore 34 of syringe 10 is filled, typically at room or ambient temperature, with a volume of the fluid 36 by introducing fluid 36 through rearward opening 28 of the tubular barrel 12 and then inserting the piston 18. Alternatively, fluid 36 may be aspirated into reservoir of the cylindrical bore 34 through the fluid outlet 24 by rearward movement of piston 18 inside the tubular barrel 12. Portions of the fluid 36 directly contact and wet the interior surface 14 or, if present, the coating 64 on the interior surface 14. The syringe 10 is placed in a refrigerated environment that is chilled to a temperature less than the freezing point of the fluid 36 and is stored indefinitely at the temperature to extend the working life of the fluid 36. For typical fluids 36, the syringe 10 and fluid 36 are frozen and stored at temperatures in the range of about −40° C. to about −80° C.

The tubular barrel 12 and the fluid 36 may shrink by different amounts when the fluid 36 is frozen to its freezing point or below due to differences in coefficients of thermal expansion. Shortly before use, the syringe 10 is removed from the refrigerated environment and warmed to ambient temperature with the goal to thaw the frozen fluid 36. For example, the syringe 10 may be placed on a bench top for a time sufficient to warm the fluid 36 to ambient temperature. The presence of the modified surface layer 60, the removal of contaminants 62, and/or the coating 64 promotes a reduction in the likelihood that, as the frozen fluid 36 thaws, air in bubbles or voids will be trapped in the fluid 36 proximate to the interior surface 14. Hence, void formation is prevented or, at the least, significantly reduced, which improves the yield of usable syringes 10.

A benefit of the modification of the interior surface 14 is that the total thickness, t, between the interior and exterior surfaces 14, 15 of the tubular barrel 12 may be a standard thickness routinely used for the syringe 10. The tubular barrel 12 does not have to be thinned to reduce the total thickness, t, so that the formation of freeze-thaw voids in fluid 35 is reduced.

Figure 4:
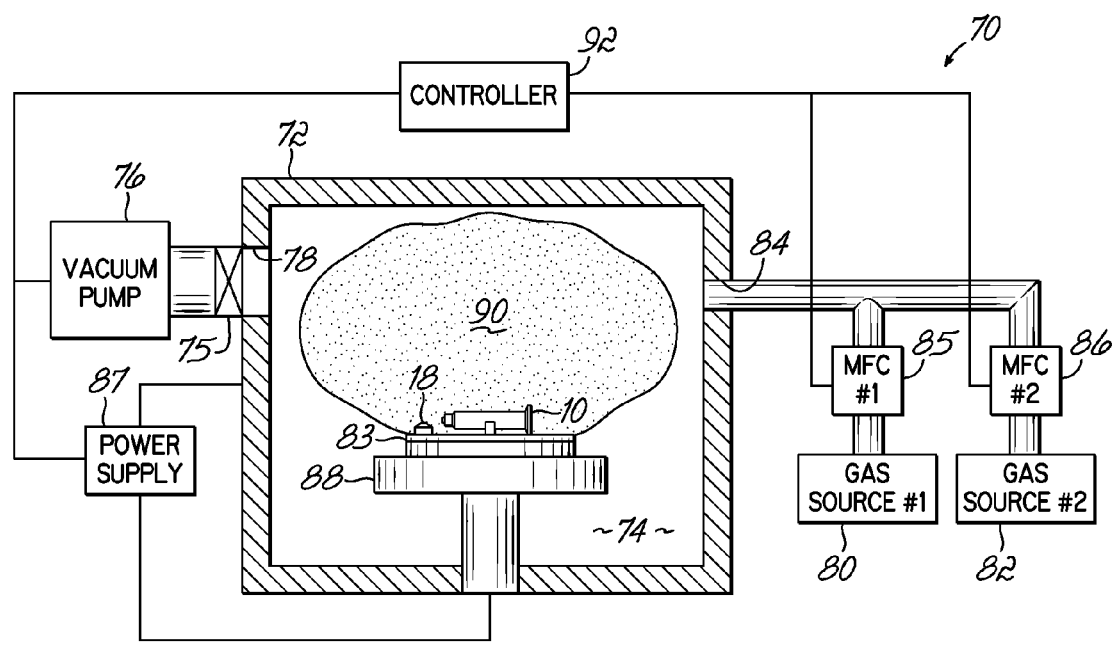
FIG. 4 is a diagrammatic view of a plasma treatment system for treating syringes with a plasma in accordance with the principles of the embodiments of the present invention.

With reference to FIG. 4, a plasma treatment system 70 may be used to form the modified surface layer 60, to deposit the coating 64, and/or to remove contaminants 62 by treating the interior surface 14 of the tubular barrel 12 with a plasma 90. Generally, a plasma treatment system 70 includes a vacuum chamber 72 constituted by walls that enclose a processing space 74. During a plasma process, the vacuum chamber 72 is sealed fluid-tight from the surrounding ambient environment that is at atmospheric pressure, evacuated to a suitable partial vacuum, and supplied with one or more process gases appropriate for the intended plasma treatment of one or more of the syringes 10. A vacuum pump 76 is used to evacuate the processing space 74 of vacuum chamber 72 through a vacuum port 78. Vacuum pump 76 may comprise one or more vacuum pumping devices with controllable pumping speeds as recognized by persons of ordinary skill in the art of vacuum technology. A gate valve 75 is disposed between the processing space 74 and the vacuum pump 76 and is used to open and close the vacuum port to regulate evacuation of the processing space 74.

Process gas sources 80, 82 are coupled with a gas inlet port 84 defined in the vacuum chamber 72. One or more working or process gases are admitted at a regulated flow rate to the processing space 74 from process gas sources 80, 82 through the gas inlet port 84. Mass flow controllers 85, 86 meter the flow of process gas from the respective process gas sources 80, 82 to the processing space 74. The gas flow rate from one or both of the process gas sources 80, 82 and the pumping rate of vacuum pump 76 are adjusted, as needed, to create a processing pressure and environment suitable for plasma generation and suitable for the intended treatment process. Processing space 74 is continuously evacuated as one or more process gases are simultaneously introduced from the process gas sources 80, 82. The result is that fresh gases are continuously exchanged within the processing space 74 when the plasma is present, and spent process gas and volatile species removed from one or more syringes 10 are eliminated from the processing space 74 through the vacuum port 76. Before the process gas(es) are introduced or contemporaneously with the introduction of one or more process gases, the vacuum pump 76 may be used to evacuate atmospheric gases from the processing space 74 after vacuum chamber 72 is vented to place the syringes 10 on a substrate support or table 83 inside the vacuum chamber 72.

The tubular barrel 12 of each syringe 10 may be oriented such that the rearward opening 28 faces toward the gas inlet port 84, as shown in the representative embodiment. However, the orientation of the barrels 12 may differ so long as the plasma 90 can penetrate into the portion of the interior surface 14 on each tubular barrel 12 that is wetted by the fluid 36 during use.

Operating pressures during plasma treatments within the vacuum chamber 72 are typically about fifty (50) mTorr to about five (5) Torr. The process gases contained in at least one of the process gas sources 80, 82 include, but are not limited, to oxygen ($O_2$), nitrous oxide (NO), ozone ($O_3$), tetrafluoromethane ($CF_4$), silanes such as tetraethoxysilane (TEOS) and $SiH_4$, dichlorodimethylsilane (DDS), methyltrichlorosilane (MTS), hexadichloromethylsilyl oxide (HDMSO), trichlorosilyldichloroborane (TDADB), 1,1,3,3-tetramethyl-disiloxane (tDMSO), octafluorocyclobutane ($C_4F_8$), a gas mixture of trifluoromethane ($CHF_3$) and $CF_4$, hexafluoroethane ($C_2F_6$), and octafluoropropane ($C_3F_8$). The process gas of one or both of the process gas sources 80, 82 may be diluted with an inert gas, such as argon (Ar), which may function to improve the spatial uniformity of the plasma treatment.

A power supply 87 is electrically coupled with, and transfers electrical power to, an electrode 88 disposed inside of the vacuum chamber 72. The table 83 is electrically coupled with the electrode 88. Power transferred from the power supply 87 to the electrode 88 is effective for forming the plasma 90 from the one or more working or process gases confined within processing space 74 and also controls the direct current (DC) self-bias. Although the invention is not so limited, the power supply 87 may be a radio-frequency (RF) power supply operating at a frequency between about 40 kHz and about 13.56 MHz, preferably about 13.56 MHz, although other frequencies may be used, and a power level, for example, between about 50 watts and about 1000 watts at 13.56 MHz. Those of ordinary skill in the art will appreciate that different treatment chamber designs may permit different bias powers.

A controller 92 is coupled to the various components of the plasma treatment system 70 to facilitate control of the plasma process. The controller 92 may be operated to continuously supply power to the plasma 90. Alternatively, the controller 92 may be operated to pulse the power supplied from the power supply 87 to the plasma 90. For example, the power supply 87 may be pulsed by the controller 92 with a duty cycle that is 0.55 msec with power applied to the electrode represented by the substrate support 88 and 1 msec with no applied power.

Plasma treatment system 70 may assume different configurations understood by those of ordinary skill in the art and, therefore, is not limited to the exemplary configuration described herein. For example, the plasma 90 may be generated remote of vacuum chamber 72 and delivered from the remote location to the processing space 74. As another example, the electrical signals from the power supply 87 may be coupled with a second discrete electrode inside the vacuum chamber 72. Plasma treatment system 70 is further understood to include components not shown in FIG. 4 that are necessary for operation of system 70.

The interior surface 14 of the tubular barrel 12 may be plasma processed inside the plasma treatment system 70 to form a modified layer in the representative form of the modified surface layer 60 and/or the coating 64, and to remove any contaminants 62. To that end, one or more of the syringes 10 are placed inside the processing space 74 and are exposed to plasma 90 generated from one or more process gases and under a recipe consisting of suitable process conditions. Among the control parameters for the plasma modification process are the flow set points for the process gases supplied from the process gas sources 80, 82 to the processing space 74, the power supplied by the power supply 87 to energize the plasma, and the exposure time of the interior surface 14 to the plasma 90. As an artifact of the plasma treatment of the interior surface 14, the exterior surface 15 of the tubular barrel 12 may also be exposed to the plasma, unless masked in some conventional manner, and thereby receive a plasma treatment similar or identical to the plasma treatment of the interior surface 14.

In one specific embodiment, the plasma 90 used to treat syringe 10 is generated from an oxygen-rich process gas, such as $O_2$, NO, or $O_3$. Although not wished to be bound by theory, it is believed that active species (e.g., radicals and ions) of oxygen from the plasma 90 are relatively effective for providing a surface modified layer by removing contaminants 62 (FIGS. 3A, 3B) from the interior surface 14 of tubular barrel 12 and/or forming the modified surface layer 60 (FIG. 3). In another embodiment, the plasma 90 used to treat syringe 10 may be formed from a gas mixture that includes, in addition to the oxygen-containing process gas, a fluorine-containing gas species like $CF_4$. Similarly, it is believed that active species of fluorine originating from the plasma 90 may assist the active species of oxygen in modifying the interior surface 14 to form the modified surface layer 60. The gas mixture used to generate the plasma 90 may further include an inert gas, such as Ar, as a diluent, supplied from another gas source (not shown) or mixed directly with the process gas of the gas sources 80, 82.

An exemplary set of process conditions include a process gas of $O_2$ supplied at about 130 standard cubic centimeters per minute (sccm), a pressure of about 200 mTorr in the processing space 74, a power of about 400 watts, and an exposure time of about 300 seconds. Another exemplary set of process conditions include a gas mixture of $O_2$ supplied at about 50 sccm and $CF_4$ supplied at about 200 sccm (i.e., about 20 percent by volume of $O_2$), a pressure of about 310 mTorr in the processing space 74, a power of about 400 watts, and an exposure time of about 300 seconds.

In an alternative embodiment, the plasma 90 to which the one or more syringes 10 residing inside the processing space 74 are exposed may be generated from a process gas or a mixture of process gases capable of forming the coating 64 (FIG. 3C). The coating 64 may be deposited on the interior surface 14 after the modified surface layer 60 is formed and/or after the contaminants 62 are removed. Alternatively, the coating 64 may be deposited directly on the interior surface 14 with no prior plasma treatment intended to form layer 60 or remove contaminants 62.

The coating 64 may formed using a process gas with a composition suitable to form a thin film or layer of a material capable effective to prevent or, at the least, significantly reduce void formation in fluid 36 when the syringe 10 and fluid 36 are frozen and thawed. Exemplary process gases include, but are not limited to, a silicon-containing material, such as silanes like TEOS, $SiH_4$, DDS, MTS, HDMSO, TDADB, or TDMSO, that are capable of forming a silicon-containing thin film, such as a polysiloxane material, that operates as coating 64. Other exemplary process gases that may be used to generate the plasma to which the interior surface 14 is exposed include, but are not limited to, fluorinated hydrocarbon compounds like $C_4F_8$, a gas mixture of $CHF_3$ and $CF_4$, $C_2F_4$, $C_2F_6$, or $C_3F_8$, that are capable of forming a fluorine-containing thin film that operates as coating 64. The fluorine-containing thin film constituting coating 64 may have Teflon®-like properties. If the coating 64 is deposited after the modified surface layer 60 is formed and/or after the contaminants 62 are removed, the change in the gas mixture may be accomplished without breaking vacuum and, preferably, without extinguishing the plasma 90 inside vacuum chamber 72 so that the interior surface 14 is not exposed to the ambient environment before the coating 64 is applied.

An exemplary set of process conditions include a process gas of $C_4F_8$ supplied at about 250 sccm, a pressure of about 100 mTorr in the processing space 74, a power of about 300 watts, and an exposure time of about 300 seconds. The power may be pulsed with a duty cycle in which power is applied for about 0.55 msec and power is not applied for about 1 msec. Another exemplary set of process conditions include a process gas of TMDSO supplied at about 125 sccm, a pressure of about 65 mTorr in the processing space 74, a power of about 200 watts, and an exposure time of about 300 seconds with the power continuously applied.

The invention also contemplates that at least the fluid-contact surface 32 of the piston 18 may be plasma treated in a manner similar to the interior surface 14 of the tubular barrel 12. In particular, the fluid-contact surface 32 of the piston 18 may be exposed to a plasma, which is similar or identical to plasma 90, to form a modified surface layer similar or identical to the modified surface layer 60, to deposit a similar or coating identical to the coating 64, and/or to remove contaminants similar or identical to contaminants 62. One or more pistons 18 may be treated concurrently with one or more barrels 12 inside the processing space 74.

It will be understood that when an element as a layer, region or substrate is described as being "on" or "over" another element, it can be directly on or over the other element or intervening elements may also be present. In contrast, when an element is described as being "directly on" or "directly over" another element, there are no intervening elements present. It will also be understood that when an element is described as being "attached", "connected", or "coupled" to another element, it can be directly connected or coupled to the other element or intervening elements may be present. In contrast, when an element is described as being "directly attached", "directly connected", or "directly coupled" to another element, there are no intervening elements present.

While the invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. For example, the syringes 10 of the invention may be applicable for use with medical fluids, silicones, and other types of fluids that are frozen when inside the reservoir of the cylindrical bore 34 beyond applications relating to semiconductor and optoelectronic packaging. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A syringe for use with a fluid susceptible to freeze-thaw void formation, the syringe comprising:
    a tubular barrel having a cylindrical bore configured to contain the fluid, said cylindrical bore having an interior surface configured to be contacted by the fluid, and said interior surface treated with a plasma.

2. The syringe of claim 1 wherein said interior surface includes a coating formed by the plasma, and said coating is contacted by the fluid.

3. The syringe of claim 2 wherein said coating includes a silicon-containing material or a fluorine-containing material.

4. The syringe of claim 1 wherein said tubular barrel includes a surface layer modified by the plasma, and the surface layer extends to intersect said interior surface.

5. The syringe of claim 1 wherein said tubular barrel includes a first opening and a second opening, and further comprising:
    a piston located between said first opening and said second opening, said piston including a fluid-contact surface that is contacted by the fluid contained by said cylindrical bore, and said fluid-contact surface treated with the plasma.

6. The syringe of claim 1 further comprising:
    a fluid selected from the group consisting of premixed curable liquids, epoxies, pastes, thixotropic liquids, adhesives, and liquids having a viscosity ranging from 1 centipoise to 1,000,000 centipoise.

7. The syringe of claim 1 wherein said tubular barrel is composed of a polymer that contains an agent, and said tubular barrel proximate to said interior surface is depleted of said agent after said interior surface is treated with the plasma.

* * * * *

UNITED STATES PATENT AND TRADEMARK OFFICE
CERTIFICATE OF CORRECTION

PATENT NO. : 8,313,455 B2
APPLICATION NO. : 13/482286
DATED : November 20, 2012
INVENTOR(S) : Henry Digregorio et al.

Page 1 of 1

It is certified that error appears in the above-identified patent and that said Letters Patent is hereby corrected as shown below:

At column 1, line 12, change "disclosures" to --disclosure--.

At column 4, line 11, change "complementarily" to --complementary-- and at line 40, change "centimeters" to --centimeter--.

At column 9, line 29, change two instances of "are" to --is--.

At column 10, line 15, after "may", insert --be-- and at line 16, after "material", delete "capable" and at line 28, change "are" to --is-- and at line 39, change "include" to --includes-- and at line 45, change "include" to --includes--.

At column 12, claim 5, line 17, after "surface" insert --is--.

Signed and Sealed this
Nineteenth Day of February, 2013

Teresa Stanek Rea
*Acting Director of the United States Patent and Trademark Office*